(12) United States Patent
Fischer et al.

(10) Patent No.: US 7,625,996 B2
(45) Date of Patent: Dec. 1, 2009

(54) METHOD FOR THE PRODUCTION OF CONJUGATES OF INSULIN-LIKE GROWTH FACTOR-1 AND POLY(ETHYLENE GLYCOL)

(75) Inventors: Stephan Fischer, Polling (DE); Friederike Hesse, Munich (DE); Hendrik Knoetgen, Penzberg (DE); Kurt Lang, Penzberg (DE); Friedrich Metzger, Freiburg (DE); Joerg Thomas Regula, Munich (DE); Christian Schantz, Munich (DE); Andreas Schaubmar, Penzberg (DE); Hans-Joachim Schoenfeld, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 22 days.

(21) Appl. No.: 11/846,857

(22) Filed: Aug. 29, 2007

(65) Prior Publication Data

US 2008/0119409 A1     May 22, 2008

(30) Foreign Application Priority Data

Aug. 31, 2006 (EP) ................... 06018170

(51) Int. Cl.
*A61K 38/30* (2006.01)
*A61K 38/00* (2006.01)

(52) U.S. Cl. ................ 530/303; 530/323; 530/333; 530/344; 530/345; 514/3

(58) Field of Classification Search ................ None
See application file for complete search history.

(56) References Cited

U.S. PATENT DOCUMENTS

| 5,158,875 | A |   | 10/1992 | Miller et al. |
| 5,427,927 | A |   | 6/1995 | Meyer et al. |
| 2003/0204864 | A1 | * | 10/2003 | Daniell ................ 800/278 |
| 2004/0136952 | A1 | * | 7/2004 | Bhaskaran et al. ......... 424/85.1 |

FOREIGN PATENT DOCUMENTS

| EP | 0123228 | 10/1984 |
| EP | 0128733 | 12/1984 |
| EP | 0972838 | 1/2000 |
| EP | 1674113 | 6/2006 |
| WO | WO 91/02807 | 3/1991 |
| WO | WO 91/11520 | 8/1991 |
| WO | WO 94/12219 | 6/1994 |
| WO | WO 95/32003 | 11/1995 |
| WO | WO 2004/060300 | 7/2004 |
| WO | WO 2006/066891 | 6/2006 |

OTHER PUBLICATIONS

Pohlner et al., Bio/Technology, Nature Publishing Co. NY, US, vol. 10, Jul. 1, 1992 pp. 799-804, 1992.
Carro et al., Nat. Med. 8 (2002) pp. 1390-1397.
Dore et al., Ann. NY Acad. Sci 890 (1999) pp. 356-364.
Dore et al., Proc. Natl. Acad. Sci. USA 94 (1997) pp. 4772-4777.
Lebouc et al., FEBS Lett. 196 (1986) pp. 108-112.
Monfardini et al., Bioconjugate Chem. 6 (1995) pp. 62-69.
Pohlner et al. Nature 325 (1987) pp. 458-462.
Veronese F. M. Biomaterials 22(2001) pp. 405-417.

* cited by examiner

*Primary Examiner*—Maryam Monshipouri
*Assistant Examiner*—Samuel W. Liu
(74) *Attorney, Agent, or Firm*—George W. Johnston; Patricia S. Rocha-Tramaloni; Gene J. Yao

(57) ABSTRACT

The present invention relates to a fusion protein comprising IGF-I or an IGF-I variant N-terminally linked to the C-terminus of a propeptide. The invention relates also to a method involving the use of the aforementioned fusion protein in the production of a lysine-PEGylated IGF-I or IGF-I variant. The method comprises the steps of cultivating a prokaryotic host cell comprising an expression vector containing a nucleic acid encoding the fusion protein and causing the cell to express the fusion protein, recovering and PEGylating said fusion protein, cleaving said PEGylated fusion protein with IgA protease, and recovering lysine-PEGylated IGF-I or IGF-I variant. The invention relates also to a lysine-PEGylated IGF-I or IGF-I variant produced using the above method. In addition, the invention relates to a method for treating a neurodegenerative disorders like Alzheimer's Disease using the lysine-PEGylated IGF-I or IGF-I variant and a composition comprising the lysine-PEGylated IGF-I or IGF-I variant.

9 Claims, 4 Drawing Sheets

```
                       SEQUENCE LISTING

<160> NUMBER OF SEQ ID NOS: 36

<210> SEQ ID NO 1
   <211> LENGTH: 70
   <212> TYPE: PRT
   <213> ORGANISM: Homo sapiens

<400> SEQUENCE: 1

Gly Pro Glu Thr Leu Cys Gly Ala Glu Leu Val Asp Ala Leu Gln Phe
   1               5                   10                  15

Val Cys Gly Asp Arg Gly Phe Tyr Phe Asn Lys Pro Thr Gly Tyr Gly
               20                  25                  30

Ser Ser Ser Arg Arg Ala Pro Gln Thr Gly Ile Val Asp Glu Cys Cys
           35                  40                  45

Phe Arg Ser Cys Asp Leu Arg Arg Leu Glu Met Tyr Cys Ala Pro Leu
       50                  55                  60

Lys Pro Ala Lys Ser Ala
   65                  70

<210> SEQ ID NO 2
   <211> LENGTH: 89
   <212> TYPE: PRT
   <213> ORGANISM: Artificial Sequence
   <220> FEATURE:
   <223> OTHER INFORMATION: Description of Artificial Sequence: Synthetic
         fusion protein px3036_IAG_R K27R K65R K68

<400> SEQUENCE: 2

Met His His His His His Arg Ala Arg Arg Phe Arg Arg His Pro
   1               5                   10                  15

Arg Pro Pro Gly Pro Glu Thr Leu Cys Gly Ala Glu Leu Val Asp Ala
               20                  25                  30

Leu Gln Phe Val Cys Gly Asp Arg Gly Phe Tyr Phe Asn Arg Pro Thr
           35                  40                  45

Gly Tyr Gly Ser Ser Ser Arg Arg Ala Pro Gln Thr Gly Ile Val Asp
       50                  55                  60

Glu Cys Cys Phe Arg Ser Cys Asp Leu Arg Arg Leu Glu Met Tyr Cys
   65                  70                  75                  80

Ala Pro Leu Arg Pro Ala Lys Ser Ala
                       85
```

<210> SEQ ID NO 3
<211> LENGTH: 88
<212> TYPE: PRT
<213> ORGANISM: Artificial Sequence
<220> FEATURE:
<223> OTHER INFORMATION: Description of Artificial Sequence: Synthetic
fusion protein px3036_IAEE_F1 K27R K65R K68

<400> SEQUENCE: 3

```
Met Ser His His His His His Asn His Asn Arg Glu His Pro Arg
1               5                   10                  15

Pro Pro Gly Pro Glu Thr Leu Cys Gly Ala Glu Leu Val Asp Ala Leu
            20                  25                  30

Gln Phe Val Cys Gly Asp Arg Gly Phe Tyr Phe Asn Arg Pro Thr Gly
        35                  40                  45

Tyr Gly Ser Ser Ser Arg Arg Ala Pro Gln Thr Gly Ile Val Asp Glu
    50                  55                  60

Cys Cys Phe Arg Ser Cys Asp Leu Arg Arg Leu Glu Met Tyr Cys Ala
65                  70                  75                  80

Pro Leu Arg Pro Ala Lys Ser Ala
                85
```

<210> SEQ ID NO 4
<211> LENGTH: 87
<212> TYPE: PRT
<213> ORGANISM: Artificial Sequence
<220> FEATURE:
<223> OTHER INFORMATION: Description of Artificial Sequence: Synthetic
fusion protein px3036_IAFX_F1 K27R K65R K68

<400> SEQUENCE: 4

```
Met Asn His His His His His His Ile Glu Gly Arg His Pro Arg Pro
1               5                   10                  15

Pro Gly Pro Glu Thr Leu Cys Gly Ala Glu Leu Val Asp Ala Leu Gln
            20                  25                  30

Phe Val Cys Gly Asp Arg Gly Phe Tyr Phe Asn Arg Pro Thr Gly Tyr
        35                  40                  45

Gly Ser Ser Ser Arg Arg Ala Pro Gln Thr Gly Ile Val Asp Glu Cys
    50                  55                  60

Cys Phe Arg Ser Cys Asp Leu Arg Arg Leu Glu Met Tyr Cys Ala Pro
65                  70                  75                  80

Leu Arg Pro Ala Lys Ser Ala
                85
```

<210> SEQ ID NO 5
<211> LENGTH: 90
<212> TYPE: PRT
<213> ORGANISM: Artificial Sequence
<220> FEATURE:
<223> OTHER INFORMATION: Description of Artificial Sequence: Synthetic
fusion protein px3036_IAFX_F2 K27R K65R K68

<400> SEQUENCE: 5

```
Met Asn His His His His His His Thr Glu Phe Glu Asn Ile Glu His
1               5                   10                  15

Pro Arg Pro Pro Gly Pro Glu Thr Leu Cys Gly Ala Glu Leu Val Asp
            20                  25                  30

Ala Leu Gln Phe Val Cys Gly Asp Arg Gly Phe Tyr Phe Asn Arg Pro
        35                  40                  45

Thr Gly Tyr Gly Ser Ser Ser Arg Arg Ala Pro Gln Thr Gly Ile Val
    50                  55                  60
```

```
Asp Glu Cys Cys Phe Arg Ser Cys Asp Leu Arg Arg Leu Glu Met Tyr
 65                  70                  75                  80

Cys Ala Pro Leu Arg Pro Ala Lys Ser Ala
                 85                  90

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 6

Lys Ala Lys Arg Phe Lys Lys His
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 7

Arg Ala Arg Arg Phe Arg Arg His
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 8

Asn Thr Glu His Asn Arg Glu His
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 9

Ile Glu Gly Arg His
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 10

Thr Glu Phe Glu Asn Ile Glu His
1               5

<210> SEQ ID NO 11
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      cleavage peptide

<400> SEQUENCE: 11

Pro Arg Pro Pro Gly Pro
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      cleavage peptide

<400> SEQUENCE: 12

Ala Pro Arg Pro
1

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      cleavage peptide

<400> SEQUENCE: 13

Pro Ala Pro Arg Pro
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      cleavage peptide

<400> SEQUENCE: 14

Pro Ala Pro Gly Pro
1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      cleavage peptide

<400> SEQUENCE: 15

Pro Pro Gly Pro
1

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      cleavage peptide

<400> SEQUENCE: 16
```

```
Pro Arg Pro Pro Gly Pro
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      cleavage peptide

<400> SEQUENCE: 17

Ala Pro Arg Pro Pro Gly Pro
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      cleavage peptide

<400> SEQUENCE: 18

Pro Ala Pro Arg Pro Pro Gly Pro
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser His His His His His His
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn His His His His His His
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

His His His His His His
1               5

<210> SEQ ID NO 22
<211> LENGTH: 89
<212> TYPE: PRT
<213> ORGANISM: Artificial Sequence
<220> FEATURE:
```

<223> OTHER INFORMATION: Description of Artificial Sequence: Synthetic
    fusion protein px3036_IAG_R K27R K65 K68R

<400> SEQUENCE: 22

Met His His His His His His Arg Ala Arg Arg Phe Arg Arg His Pro
1               5                   10                  15

Arg Pro Pro Gly Pro Glu Thr Leu Cys Gly Ala Glu Leu Val Asp Ala
            20                  25                  30

Leu Gln Phe Val Cys Gly Asp Arg Gly Phe Tyr Phe Asn Arg Pro Thr
        35                  40                  45

Gly Tyr Gly Ser Ser Ser Arg Arg Ala Pro Gln Thr Gly Ile Val Asp
    50                  55                  60

Glu Cys Cys Phe Arg Ser Cys Asp Leu Arg Arg Leu Glu Met Tyr Cys
65                  70                  75                  80

Ala Pro Leu Lys Pro Ala Arg Ser Ala
                85

<210> SEQ ID NO 23
<211> LENGTH: 88
<212> TYPE: PRT
<213> ORGANISM: Artificial Sequence
<220> FEATURE:
<223> OTHER INFORMATION: Description of Artificial Sequence: Synthetic
    fusion protein px3036_IAEE_F1 K27R K65 K68R

<400> SEQUENCE: 23

Met Ser His His His His His His Asn His Asn Arg Glu His Pro Arg
1               5                   10                  15

Pro Pro Gly Pro Glu Thr Leu Cys Gly Ala Glu Leu Val Asp Ala Leu
            20                  25                  30

Gln Phe Val Cys Gly Asp Arg Gly Phe Tyr Phe Asn Arg Pro Thr Gly
        35                  40                  45

Tyr Gly Ser Ser Ser Arg Arg Ala Pro Gln Thr Gly Ile Val Asp Glu
    50                  55                  60

Cys Cys Phe Arg Ser Cys Asp Leu Arg Arg Leu Glu Met Tyr Cys Ala
65                  70                  75                  80

Pro Leu Lys Pro Ala Arg Ser Ala
                85

<210> SEQ ID NO 24
<211> LENGTH: 87
<212> TYPE: PRT
<213> ORGANISM: Artificial Sequence
<220> FEATURE:
<223> OTHER INFORMATION: Description of Artificial Sequence: Synthetic
    fusion protein px3036_IAFX_F1 K27R K65 K68R

<400> SEQUENCE: 24

Met Asn His His His His His His Ile Glu Gly Arg His Pro Arg Pro
1               5                   10                  15

Pro Gly Pro Glu Thr Leu Cys Gly Ala Glu Leu Val Asp Ala Leu Gln
            20                  25                  30

Phe Val Cys Gly Asp Arg Gly Phe Tyr Phe Asn Arg Pro Thr Gly Tyr
        35                  40                  45

Gly Ser Ser Ser Arg Arg Ala Pro Gln Thr Gly Ile Val Asp Glu Cys
    50                  55                  60

Cys Phe Arg Ser Cys Asp Leu Arg Arg Leu Glu Met Tyr Cys Ala Pro
65                  70                  75                  80

Leu Lys Pro Ala Arg Ser Ala

<210> SEQ ID NO 25
<211> LENGTH: 90
<212> TYPE: PRT
<213> ORGANISM: Artificial Sequence
<220> FEATURE:
<223> OTHER INFORMATION: Description of Artificial Sequence: Synthetic fusion protein px3036_IAFX_F2 K27R K65 K68R

<400> SEQUENCE: 25

```
Met Asn His His His His His His Thr Glu Phe Glu Asn Ile Glu His
1               5                   10                  15

Pro Arg Pro Pro Gly Pro Glu Thr Leu Cys Gly Ala Glu Leu Val Asp
                20                  25                  30

Ala Leu Gln Phe Val Cys Gly Asp Arg Gly Phe Tyr Phe Asn Arg Pro
            35                  40                  45

Thr Gly Tyr Gly Ser Ser Ser Arg Arg Ala Pro Gln Thr Gly Ile Val
        50                  55                  60

Asp Glu Cys Cys Phe Arg Ser Cys Asp Leu Arg Arg Leu Glu Met Tyr
65                  70                  75                  80

Cys Ala Pro Leu Lys Pro Ala Arg Ser Ala
                85                  90
```

<210> SEQ ID NO 26
<211> LENGTH: 70
<212> TYPE: PRT
<213> ORGANISM: Artificial Sequence
<220> FEATURE:
<223> OTHER INFORMATION: Description of Artificial Sequence: Synthetic construct

<400> SEQUENCE: 26

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Arg Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Ala Lys Ser Ala
65                  70
```

<210> SEQ ID NO 27
<211> LENGTH: 70
<212> TYPE: PRT
<213> ORGANISM: Artificial Sequence
<220> FEATURE:
<223> OTHER INFORMATION: Description of Artificial Sequence: Synthetic construct

<400> SEQUENCE: 27

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Arg Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60
```

```
Lys Pro Ala Arg Ser Ala
 65                  70

<210> SEQ ID NO 28
<211> LENGTH: 70
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 28

Gly Pro Glu Thr Leu Cys Gly Ala Glu Leu Val Asp Ala Leu Gln Phe
  1               5                  10                  15

Val Cys Gly Asp Arg Gly Phe Tyr Phe Asn Arg Pro Thr Gly Tyr Gly
             20                  25                  30

Ser Ser Ser Arg Arg Ala Pro Gln Thr Gly Ile Val Asp Glu Cys Cys
         35                  40                  45

Phe Arg Ser Cys Asp Leu Arg Arg Leu Glu Met Tyr Cys Ala Pro Leu
     50                  55                  60

Arg Pro Ala Lys Ser Ala
 65                  70

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Pro Arg Pro Pro
  1

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Pro Ala Pro Ser Pro
  1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Ala Pro Pro Ser Pro
  1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                             -continued peptide

<400> SEQUENCE: 32

Pro Arg Pro Pro Ala Pro
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Arg Pro Pro Ser Pro
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Pro Arg Pro Pro Thr Pro
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Pro Thr Pro Ser Pro
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Thr Pro Pro Thr Pro
1               5
```

METHOD FOR THE PRODUCTION OF CONJUGATES OF INSULIN-LIKE GROWTH FACTOR-1 AND POLY(ETHYLENE GLYCOL)

PRIORITY TO RELATED APPLICATIONS

This application claims the benefit of European Patent Application No. 06018170.8, filed Aug. 31, 2006, which is hereby incorporated by reference in its entirety.

FIELD OF THE INVENTION

This invention relates to a conjugate of insulin-like growth factor-I (IGF-I) or a variant thereof with poly(ethylene glycol) (PEG), a method for the production of such a conjugate, a composition comprising such a conjugate, a method for the use of such a conjugate, and a fusion protein comprising IGF-I or an IGF-I variant N-terminally linked to the C-terminus of a propeptide which may be used in the method for making the above conjugate.

BACKGROUND OF THE INVENTION

Alzheimer's disease (AD) is an increasingly prevalent form of neurodegeneration that accounts for approximately 50%-60% of the overall cases of dementia among people over 65 years of age. It currently affects an estimated 15 million people worldwide and, owing to the relative increase of elderly people in the population, its prevalence is likely to increase over the next 2 to 3 decades. AD is a progressive disorder with a mean duration of around 8.5 years between onset of clinical symptoms and death. Death of pyramidal neurons and loss of neuronal synapses in brain regions associated with higher mental functions results in the typical symptoms, characterized by gross and progressive impairment of cognitive function (Francis, P. T., et al., J. Neurol. Neurosurg. Psychiatry 66 (1999) 137-147). AD is the most common form of both senile and presenile dementia in the world and is recognized clinically as relentlessly progressive dementia that presents with increasing loss of memory, intellectual function and disturbances in speech (Merritt, A Textbook of Neurology, 6th ed., Lea & Febiger, Philadelphia (1979), pp. 484-489). Neuropathologically, the major hallmarks of AD are the presence of two characteristic lesions: the amyloid senile plaque and neurofibrillary tangle (NFT). While the plaque is deposited extraneuronally, the tangle is observed intraneuronally in the post-mortem brain. One of the major components of the amyloid plaque core is the pathologically deposited small amyloid-beta-peptide (Aβ), which is cleaved by secretases from amyloid precursor protein (APP) (Selkoe, D. J., Physiol. Rev. 81 (2001) 741-766; Hardy, J. and Selkoe, D. J., Science 297 (2002) 353-356; Bush, A. I. and Tanzi, R. E., Proc. Natl. Acad. Sci. USA 99 (2002) 7317-7319). Aβ (Abeta), a self-aggregating peptide of 39-43 residues (MW ~4 kDa), is synthesized as part of the larger APP (110-120 kDa). APP is a type I integral membrane glycoprotein with a large N-terminal extracellular domain, a single transmembrane domain and a short cytoplasmic tail. The Aβ region spans portions of the extracellular and transmembrane domains of APP. The most common hypothesis for the participation of APP in neuronal cell death in AD is the amyloid hypothesis. This hypothesis postulates that plaque amyloid depositions or partially aggregated soluble Aβ trigger a neurotoxic cascade, thereby causing neurodegeneration similar to AD pathology (Selkoe, D. J., Physiol. Rev. 81 (2001) 741-766; Hardy, J. and Selkoe, D. J., Science 297 (2002) 353-356).

Human insulin-like growth factor I (IGF-I) is a circulating hormone structurally related to insulin. IGF-I was traditionally considered the major mediator of the actions of growth hormone on peripheral tissues. IGF-I consists of 70 amino acids and is also named somatomedin C and defined by SwissProt No. P01343. Use, activity and production are mentioned in, e.g., le Bouc, Y., et al., FEBS Lett. 196 (1986) 108-112; de Pagter-Holthuizen, P., et al., FEBS Lett. 195 (1986) 179-184; Sandberg Nordqvist, A. C., et al., Brain Res. Mol. Brain Res. 12 (1992) 275-277; Steenbergh, P. H., et al., Biochem. Biophys. Res. Commun. 175 (1991) 507-514; Tanner, J. M., et al., Acta Endocrinol. (Copenh.) 84 (1977) 681-696; Uthne, K., et al., J. Clin. Endocrinol. Metab. 39 (1974) 548-554; EP 0 123 228; EP 0 128 733; U.S. Pat. No. 5,861,373; U.S. Pat. No. 5,714,460; EP 0 597 033; WO 02/32449; WO 93/02695.

The regulation of IGF-I function is quite complex. In the circulation, only 0.2% of IGF-I exists in the free form whereas the majority is bound to IGF-binding proteins (IGFBP's), which have very high affinities to IGF's and modulate IGF-I function. The factor can be locally liberated by mechanisms releasing IGF-I such as proteolysis of IGFBPs by proteases.

IGF-I plays a paracrine role in the developing and mature brain (Werther, G. A., et al., Mol. Endocrinol. 4 (1990) 773-778). In vitro studies indicate that IGF-I is a potent non-selective trophic agent for several types of neurons in the CNS (Knusel, B., et al., J. Neurosci. 10(1990) 558-570; Svrzic, D., and Schubert, D., Biochem. Biophys. Res. Commun. 172 (1990) 54-60), including dopaminergic neurons (Knusel, B., et al., J. Neurosci. 10(1990) 558-570) and oligodendrocytes (McMorris, F. A., and Dubois-Dalcq, M., J. Neurosci. Res. 21 (1988) 199-209; McMorris, F. A., et al., Proc. Natl. Acad. Sci. USA 83 (1986) 822-826; Mozell, R. L., and McMorris, F. A., J. Neurosci. Res. 30 (1991) 382-390)). U.S. Pat. No. 5,093,317 mentions that the survival of cholinergic neuronal cells is enhanced by administration of IGF-I. It is further known that IGF-I stimulate peripheral nerve regeneration (Kanje, M., et al., Brain Res. 486 (1989) 396-398) and enhance ornithine decarboxylase activity U.S. Pat. No. 5,093,317). U.S. Pat. No. 5,861,373 and WO 93/02695 mention a method of treating injuries to or diseases of the central nervous system that predominantly affects glia and/or non-cholinergic neuronal cells by increasing the active concentration(s) of IGF-I and/or analogues thereof in the central nervous system of the patient. WO 02/32449 is directed to methods for reducing or preventing ischemic damage in the central nervous system of a mammal by administering to the nasal cavity of the mammal a pharmaceutical composition comprising a therapeutically effective amount of IGF-I or biologically active variant thereof. The IGF-I or variant thereof is absorbed through the nasal cavity and transported into the central nervous system of the mammal in an amount effective to reduce or prevent ischemic damage associated with an ischemic event. EP 0 874 641 claims the use of an IGF-I or an IGF-II for the manufacture of a medicament for treating or preventing neuronal damage in the central nervous system, due to AIDS-related dementia, AD, Parkinson's Disease, Pick's Disease, Huntington's Disease, hepatic encephalopathy, cortical-basal ganglionic syndromes, progressive dementia, familial dementia with spastic parapavresis, progressive supranuclear palsy, multiple sclerosis, cerebral sclerosis of Schilder or acute necrotizing hemorrhagic encephalomyelitis, wherein the medicament is in a form for parenteral administration of an effective amount of said IGF outside the blood-brain barrier or blood-spinal cord barrier.

Reduction of brain and serum levels of free IGF-I has been related to the pathogenesis of sporadic and familial forms of AD. Furthermore, IGF-I protects neurons against Aβ-induced neurotoxicity (Niikura, T., et al., J. Neurosci. 21 (2001) 1902-1910; Dore, S., et al., Proc. Natl. Acad. Sci. USA 94 (1997) 4772-4777; Dore, S., et al., Ann. NY Acad. Sci. 890 (1999) 356-364). Recently, it was shown that peripherally administered IGF-I is capable of reducing brain Aβ levels in rats and mice (Carro, E., et al., Nat. Med. 8 (2002) 1390-1397). Furthermore, the study demonstrated that in a transgenic AD mouse model prolonged IGF-I treatment significantly reduced brain amyloid plaque load. These data strongly support the idea that IGF-I is able to reduce brain Aβ levels and plaque-associated brain dementia by clearing Aβ from the brain.

Covalent modification of proteins with poly(ethylene glycol) (PEG) has proven to be a useful method to extend the circulating half-lives of proteins in the body (Hershfield, M. S., et al., N. Engl. J. Med. 316 (1987) 589-596; Meyers, F. J., et al., Clin. Pharmacol. Ther. 49 (1991) 307-313; Delgado, C., et al., Crit. Rev. Ther. Drug Carrier Syst. 9 (1992) 249-304; Katre, Advanced Drug Delivery Reviews 10 (1993) 91-114; EP-A 0400472; Monfardini, C., et al., Bioconjugate Chem. 6 (1995) 62-69; Satake-Ishikawa, R., et al., Cell Struct. Funct. 17 (1992) 157-160; Katre, N. V., et al., Proc. Natl. Acad. Sci. USA 84 (1987) 1487-1491; Tsutsumi, Y., et al., Jpn. J. Cancer Res. 85 (1994) 9-12; Inoue, H., et al., J. Lab. Clin. Med. 124 (1994) 529-536; Chamow, S. M., et al., Bioconjugate Chem. 5 (1994) 133-140).

Other advantages of PEGylation are an increase of solubility and a decrease in protein immunogenicity (Katre, N. V., J. Immunol. 144 (1990) 209-213). A method for the PEGylation of proteins is the use of poly(ethylene glycol) activated with amino-reactive reagents like N-hydroxysuccinimide (NHS). With such reagents poly(ethylene glycol) is attached to the proteins at free primary amino groups such as the N-terminal α-amino group and the ε-amino groups of lysine residues. A limitation of this approach is that proteins typically contain a considerable amount of lysine residues and therefore the poly(ethylene glycol) groups are attached to the protein in a non-specific manner at all of the free ε-amino groups, resulting in a heterologous product mixture of random PEGylated proteins. Therefore, NHS-PEGylated proteins can be unsuitable for commercial use because of low specific activity. Inactivation results from covalent modification of one or more lysine residues or the N-terminal amino residue required for biological activity or from covalent attachment of the poly(ethylene glycol) residues near or at the active site of the protein. For example, it was found that modification of human growth hormone using NHS-PEGylation reagents reduces the biological activity of the protein by more than 10-fold (Clark, R., et al., J. Biol. Chem. 271 (1996) 21969-21977). Human growth hormone contains 9 lysines in addition to the N-terminal amino acid. Certain of these lysines are located in regions of the protein known to be critical for receptor binding (Cunningham, B. C., et al., Science 254 (1991) 821-825). In addition, the modification of erythropoietin by the use of amino-reactive poly(ethylene glycol) reagents results also in a nearly complete loss of biological activity (Wojchowski, D. M., et al., Biochim. Biophys. Acta 910 (1987) 224-232). Covalent modification of Interferon-α2 with amino-reactive PEGylation reagents results in 40-75% loss of bioactivity (U.S. Pat. No. 5,382,657). A similar modification of G-CSF results in greater than 60% loss of activity (Tanaka, H., et al., Cancer Res. 51 (1991) 3710-3714) and of Interleukin-2 in greater than 90% loss of bioactivity (Goodson, R. J., and Katre, N. V., BioTechnology 8 (1990) 343-346).

WO 94/12219 and WO 95/32003 claim polyethylene glycol conjugates comprising PEG and IGF or a cystein mutated IGF, said PEG attached to said mutein at a free cystein in the N-terminal region of the mutein. WO 2004/60300 describes N-terminally PEGylated IGF-I.

The recognition site of the IgA Protease is described as Yaa-Pro.!.Xaa-Pro (as used herein, ".!." refers to the cleavage site for IgA Protease). Yaa stands for Pro (or rarely for Pro in combination with Ala, Gly or Thr: Pro-Ala, Pro-Gly, or Pro-Thr. Xaa stands for Thr, Ser or Ala (Pohlner, J., et al., Bio/Technology 10 (1992) 799-804; Pohlner, J., et al., Nature 325 (1987) 458-462; and U.S. Pat. No. 5,427,927). Natural cleavage sites have been identified by Wood, S. G. and Burton J., Infect. Immun. 59 (1991) 1818-1822. Synthetic peptide substrates for the immunoglobulin A1 protease from Neisseria gonorrhoea (type 2) are the autoproteolytic sites Lys-Pro-Ala-Pro.!.Ser-Pro, Val-Ala-Pro-Pro.!.Ser-Pro, Pro-Arg-Pro-Pro.!.Ala-Pro, Pro-Arg-Pro-Pro.!.Ser-Pro, Pro-Arg-Pro-Pro.!.Thr-Pro and the IgA1 Cleavage Sites Pro-Pro-Thr-Pro.!.Ser-Pro and Ser-Thr-Pro-Pro.!.Thr-Pro.

WO 2006/066891 discloses conjugates consisting of an insulin-like growth factor-1 (IGF-I) variant and one or two poly(ethylene glycol) group(s), characterized in that said IGF-I variant has an amino acid alteration at up to three amino acid positions 27, 37, 65, 68 of the wild-type IGF-I amino acid sequence so that one or two of said amino acids is/are lysine and amino acid 27 is a polar aminio acid but not lysine, is conjugated via the primary amino group(s) of said lysine(s) and said poly(ethylene glycol) group(s) have an overall molecular weight of from 20 to 100 kDa is disclosed. Such conjugates are useful for the treatment of neurodegenerative disorders like Alzheimer's Disease. WO 2006/074390 refers to IGF-I fusion polypeptides.

SUMMARY OF THE INVENTION

The present invention relates in part to a fusion protein which comprises IGF-I or an IGF-I variant N-terminally linked to the C-terminus of a propeptide. The C-terminus of the propeptide comprises the amino acid sequence Y-Pro, wherein Y is selected from the group consisting of: Pro-; Pro-Ala; Pro-Gly; Pro-Thr; Ala-Pro; Gly-Pro; Thr-Pro; Arg-Pro; and Pro-Arg-Pro. The animo acid residues(s) of "Y", above, constitute(s) a fragment of a lysine-free beta-galactosidase. The corresponding nucleic acid sequence encoding this fragment improves the expression of the fusion protein.

Another aspect of the present invention is a method for the production of a lysine-PEGylated IGF-I or a lysine-PEGylated IGF-I variant which comprises the steps of:
 a) cultivating a prokaryotic host cell comprising an expression vector containing a nucleic acid encoding the aforementioned fusion protein and causing said cell to express said fusion protein,
 b) recovering and PEGylating said fusion protein,
 c) cleaving said PEGylated fusion protein with IgA protease, and
 d) recovering said lysine-PEGylated IGF-I or lysine-PEGylated IGF-I variant.

A further aspect of the present invention is a lysine-PEGylated IGF-I or lysine-PEGylated IGF-I variant produced using the above method.

A further aspect of the present invention is a composition which comprises a lysine-PEGylated IGF-I or lysine-PEGylated IGF-I variant according to the invention, preferably together with a pharmaceutically acceptable carrier.

Yet another aspect of the present invention is a method for the production of the aforementioned composition.

The invention further relates to a method for the treatment of Alzheimer's disease comprising the administration of a pharmaceutically-effective amount of a lysine-PEGylated IGF-I (SEQ ID NO: 1) or a lysine-PEGylated IGF-I variant to a patient in need of such treatment.

Description of the Sequence Listing

| | |
|---|---|
| SEQ ID NO: 1 | amino acid sequence of human IGF-I (amino acids 49-118 from SwissProt P01343). |
| SEQ ID NO: 2 | amino acid sequence of fusion protein px3036_IAG_R K27R K65R K68 |
| SEQ ID NO: 3 | amino acid sequence of fusion protein px3036_IAEE_F1 K27R K65R K68 |
| SEQ ID NO: 4 | amino acid sequence of fusion protein px3036_IAFX_F1 K27R K65R K68 |
| SEQ ID NO: 5 | amino acid sequence of fusion protein px3036_IAFX_F2 K27R K65R K68 |
| SEQ ID NO: 6-10 | linker |
| SEQ ID NO: 11-18 | cleavage sequences |
| SEQ ID NO: 19-21 | sequences for use as $X_1$-$His_n$ |
| SEQ ID NO: 22 | amino acid sequence of fusion protein px3036_IAG_R K27R K65 K68R |
| SEQ ID NO: 23 | amino acid sequence of fusion protein px3036_IAEE_F1 K27R K65 K68R |
| SEQ ID NO: 24 | amino acid sequence of fusion protein px3036_IAFX_F1 K27R K65 K68R |
| SEQ ID NO: 25 | amino acid sequence of fusion protein px3036_IAFX_F2 K27R K65 K68R |
| SEQ ID NO: 26 | amino acid sequence of the IGF-I variant RKK |
| SEQ ID NO: 27 | amino acid sequence of the IGF-I variant RKR |
| SEQ ID NO: 28 | amino acid sequence of the IGF-I variant RRK |

DETAILED DESCRIPTION OF THE INVENTION

Figure 1:
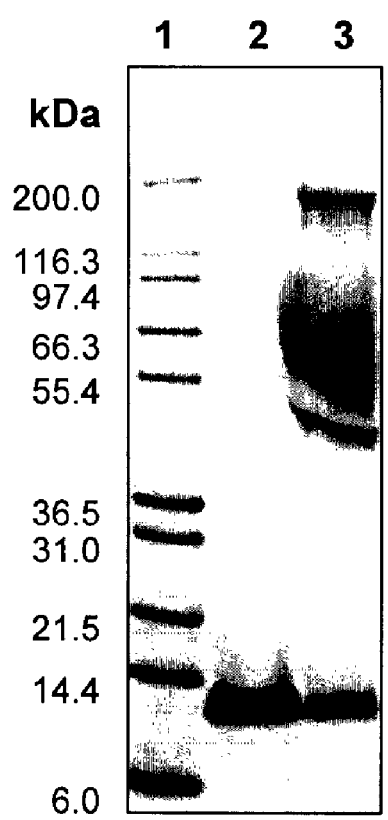
FIG. 1: Peptide analysis of monoPEGylated fusion protein.
SDS-PAGE analysis of folded fusion protein before and after PEGylation. Lane 1, mixture of standard protein (bovine lung aprotinin, 6.0 kDa; chicken egg white lysozyme, 14.4 kDa; soybean trypsin inhibitor, 21.5 kDa; bovine erythrocyte carbonic anhydrase, 31.0 kDa; porcine muscle lactate dehydrogenase, 36.5 kDa; bovine liver glutamic dehydrogenase, 55.4 kDa; bovine serum albumin, 66.3 kDa; rabbit muscle phosphorylase b, 97.4 kDa; *E. coli* β-galactosidase, 97.4 kDa; rabbit muscle myosin, 200 kDa); lane 2, pro-IGF-I before pegylation; lane 3, pro-IGF-I after pegylation.

As used herein, "IGF-I" refers to human insulin-like growth factor. It consists of 70 amino acids and has the amino acid sequence of SEQ ID NO: 1.

The present invention relates in part to a fusion protein which comprises IGF-I (SEQ ID NO: 1) or an IGF-I variant N-terminally linked to the C-terminus of a propeptide. The C-terminus of the propeptide comprises the amino acid sequence Y-Pro, wherein Y is selected from the group consisting of: Pro; Pro-Ala; Pro-Gly; Pro-Thr; Ala-Pro; Gly-Pro; Thr-Pro; Arg-Pro; Pro-Arg-Pro; Ala-Pro-Arg-Pro (SEQ ID NO: 12); and Pro-Ala-Pro-Arg-Pro (SEQ ID NO: 13). In preferred embodiments, Y is selected from the group consisting of: Pro; Pro-Ala; Arg-Pro; Pro-Arg-Pro Ala-Pro-Arg-Pro (SEQ ID NO: 12); and Pro-Ala-Pro-Arg-Pro (SEQ ID NO: 13). In especially preferred embodiments, Y is selected from the group consisting of: Pro; Pro-Arg-Pro; Ala-Pro-Arg-Pro (SEQ ID NO: 12); and Pro-Ala-Pro-Arg-Pro (SEQ ID NO: 13).

The IGF-I variant is a polypeptide consisting of 70 amino acids that differs from IGF-I (SEQ ID NO: 1) in that one or two of the lysines present at residue positions 27, 65, and 68 of IGF-I is independently substituted by a polar amino acid selected from the group consisting of: cysteine (C); aspartic acid (D); glutamic acid (E); histidine (H); asparagine (N); glutamine (Q); arginine (R); serine (S); and threonine (T). In preferred embodiments, the aforementioned lysine(s) is/are substituted with arginine(s). In each case of an IGF-I variant, the remainder of the amino acid sequence of the IGF-I variant is the same as that of IGF-I. In preferred embodiments, the polar amino acid is selected from the group consisting of: arginine; glutamine; and asparagine. In especially preferred embodiments, the polar amino acid is asparagine.

In preferred embodiments, the IGF-I variant is selected from the group consisting of: RRK, RKR, and RRK. As used herein, "RKK" refers to an IGF-I variant of SEQ ID NO: 26 and differs from IGF-I (SEQ ID NO: 1) in that it contains arginine instead of lysine at residue position 27, "RKR" refers to an IGF-I variant of SEQ ID NO: 27 and differs from IGF-I (SEQ ID NO: 1) in that it contains arginine instead of lysine at residue positions 27 and 68, and "RRK" refers to an IGF-I variant of SEQ ID NO: 28 and differs from IGF-I (SEQ ID NO: 1) in that it contains arginine instead of lysine at residue positions 27 and 65. In IGF-I, lysine is present at residue positions 27, 65, and 68 and, therefore, "KKK" may be used to refer to IGF-I.

In preferred embodiments, the propeptide does not comprise a lysine residue.

In a preferred embodiment, the fusion protein comprises up to 30 amino acids.

In a preferred embodiment, the fusion protein has the following amino acid sequence Met-$X_1$-His$_n$-$X_2$-Pro-Z wherein:
Met is a methionine residue;
$X_1$ is selected from the group consisting of: a bond, serine, or asparagine;
His is a histidine residue;
n is an integer from 0 to 10;
$X_2$ is a linker peptide having an amino acid sequence selected from the group consisting of:
SEQ ID NO: 6; SEQ ID NO: 7; SEQ ID NO: 8; SEQ ID NO: 9; and SEQ ID NO: 10;
Pro is a proline residue; and
Z is IGF-I (SEQ ID NO: 1) or an IGF-I variant as described above.

The present invention relates also to a method for the production of a lysine-PEGylated IGF-I or a lysine-PEGylated IGF-I variant. As used herein, the term "PEGylation" refers to the attachment of a PEG group or PEG groups to a molecule and a molecule is said to be "PEGylated" if it has a PEG group or PEG groups attached. "Lysine-PEGylated", when used to refer to IGF-I (SEQ ID NO: 1) or an IGF-I variant, means that the IGF-I (SEQ ID NO: 1) or IGF-I variant has a PEG group attached to a lysine residue therein. The IGF-I variant is as described above.

As used herein, "PEG" refers to poly(ethylene glycol). As used herein, the terms "poly(ethylene) glycol" and "PEG" broadly encompass any poly(ethylene glycol) molecule in which the number of ethylene glycol units is at least 460, preferably 460 to 2300 (about 20 kDa to 100 kDa) and especially preferably 460 to 1840. Poly(ethylene glycol) is a water-soluble polymer that is commercially available or can be prepared by ring-opening polymerization of ethylene glycol according to methods well known in the art (Kodera, Y., et al., Progress in Polymer Science 23 (1998) 1233-1271; Francis, G. E., et al., Int. J. Hematol. 68 (1998) 1-18). The number of ethylene glycol units in PEG is approximated for the molecular mass described in Daltons. For example, if two PEG molecules are attached to a linker where each PEG molecule has the same molecular mass of 10 kDa, then the total molecular mass of PEG on the linker is about 20 kDa. The molecular masses of the PEG attached to the linker can also be different, e.g., of two molecules on a linker one PEG molecule can be 5 kDa and one PEG molecule can be 15 kDa.

Usually PEGs which contain more than 2300 ethylene glycol units are not used. Preferably, a PEG used in the invention terminates on one end with hydroxy or methoxy (methoxy PEG, mPEG) and is, on the other end, covalently attached to a linker moiety via an ether oxygen bond. The PEG polymer is either linear or branched. Preferably the PEG polymer is branched. Branched PEGs are described, e.g., in Veronese, F. M., et al., Journal of Bioactive and Compatible Polymers 12 (1997) 196-207. Useful PEG reagents are, e.g., available from Nektar Therapeutics (www.nektar.com). Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEGs usually have 2 to 8 arms and are described in, for example, EP-A 0 473 084 and U.S. Pat. No. 5,932,462. Especially preferred are PEGs with two PEG side-chains linked via the primary amino group of a lysine (abbreviated as PEG2) (Monfardini, C., et al., Bioconjugate Chem. 6 (1995) 62-69).

It was surprisingly found that IgA protease is capable of cleaving the amino acid sequence Y-Pro.!.Gly-Pro ("!." herein and hereafter represents the cleavage position) wherein Y is as described above and Gly-Pro are the first two amino acids of IGF-I (SEQ ID NO: 1) or the IGF-I variant. As discussed above, in preferred embodiments Y is selected from the group consisting of: Pro; Pro-Ala; Pro-Gly; Pro-Thr; Ala-Pro; Gly-Pro; Thr-Pro; Arg-Pro; Pro-Arg-Pro; Ala-Pro-Arg-Pro (SEQ ID NO: 12); and Pro-Ala-Pro-Arg-Pro (SEQ ID NO: 13). Accordingly, the respective sequences around the cleavage site include: Pro-Ala-Pro.!.Gly-Pro (SEQ ID NO:14), Pro-Pro-!.Gly-Pro (SEQ ID NO:15), Pro-Arg-Pro-Pro.!. Gly-Pro (SEQ ID NO:16), Ala-Pro-Arg-Pro-Pro.!.Gly-Pro (SEQ ID NO:17) and Pro-Ala-Pro-Arg-Pro-Pro.!.Gly-Pro (SEQ ID NO:18).

In accordance with the present invention the term "IgA protease" includes proteases which specifically cleave IgA and which are described for example by Kornfeld, S. J. and Plaut, A. G. in Rev. Infekt. Dis. 3 (1981) 521-534 as e.g. IgA1 protease from Neisseria gonorrhoea (type 2). Recombinant IgA proteases such as those described in DE-A 36 22 221; Koomey, J. M., et al., Proc. Natl. Acad. Sci. USA 79 (1982) 7881-7885; Bricker, J., et al., Proc. Natl. Acad. Sci. USA 80 (1983) 2681-2685; Pohlner, J., et al., Nature 325 (1987) 458-462; and Halter, R., et al., EMBO J. 3 (1984) 1595-1601 are also just as suitable. Preferably said IgA protease is IgA protease from *Neisseria gonorrhoea*, preferably type 2.

The method of the present invention therefore relates to a method comprising the steps of expressing the aforementioned fusion protein, recovering the fusion protein, and cleaving the fusion protein using IgA protease to recover lysine-PEGylated IGF-I or lysine-PEGylated IGF-I variant.

The gene encoding the fusion protein is preferably placed under the control of suitable (preferably inducible) expression signals so that fusion proteins can be produced according to the requirements. Suitable prokaryotic or eukaryotic (plant as well as animal) cells can be used as host cells for the production of protein fusions; cell-free systems are, however, also possible.

A preferred embodiment of the process according to the present invention is characterized in that a host cell is transformed with a recombinant DNA or a recombinant vector, in which the DNA or the vector contains at least one copy of a gene which codes for a fusion protein according to the invention and the transformed cell is cultured in a suitable medium, the gene coding for the fusion protein is made to express in the transformed cell, the fusion protein is PEGylated and subsequently cleaved with IgA protease and the PEGylated IGF-I or IGF-I variant is isolated.

The method of the present invention for the production of a lysine-PEGylated IGF-I or a lysine PEGylated IGF-I variant therefore comprises the steps of:
(A) cultivating a prokaryotic host cell comprising an expression vector containing a nucleic acid encoding a fusion protein according to claim 1 and causing said cell to express said fusion protein;
(B) recovering and PEGylating said fusion protein;
(C) cleaving said PEGylated fusion protein with IgA protease, and (D) recovering said lysine-PEGylated IGF-I or lysine-PE-Gylated IGF-I variant.

It is known in the art that the production of recombinant protein in bacteria, such as *E. coli.*, may lead to the addition of a methionine residue at the N-terminus which may alter the biological activity of the protein. Moriyama et al., *Comp. Biochem. Physiol.*, 117: 201-206 (1997). An advantage to using the method of the present invention is that the resulting lysine-PEGylated IGF-I or lysine-PEGylated IGF-I variant does not have an N-terminal methionine.

The expression of the fusion protein according to the invention can, for example, be improved at the DNA level by the inclusion of fragments of lysine-free beta-galactosidase gene, i.e., Y (as defined previously) contains a part of a lysine-free beta-galactosidase protein. Other alternatives for increasing the expression of the fusion protein are known to the expert. The purification and separation of the expression product can be facilitated by the inclusion in the fusion protein of certain polypeptides, in particular, polypeptides or proteins that are highly charged (e.g. poly(Lys, Arg)) or which can bind to particular substances with high affinity (e.g. streptavidin) (see e.g. EP-A 0 089 626, EP-A 0 306 610). Especially preferred are linker peptides of SEQ ID NO: 6; SEQ ID NO: 7; SEQ ID NO: 8; SEQ ID NO: 9; and SEQ ID NO: 10; preferably N-terminally preceded by SHHHHHH (SEQ ID NO:19), NHHHHHH (SEQ ID NO:20) or HHHHHH (SEQ ID NO:21) (S=serine; N=asparagine; H=histidine)

The present invention also provides a (recombinant) nucleic acid which codes for a fusion protein according to the present invention in which an IgA protease cleavage site is incorporated in the junction region between the propeptide and the IGF-I or IGF-I variant.

A recombinant DNA according to the present invention can be obtained in a manner known to one skilled in the art of molecular biology. For this, a vector which contains a DNA sequence coding for the amino acid sequence of the IGF-I or IGF-I variant is usually cleaved with restriction endonuclease(s) in the region of the 5' end of this gene and religated with oligonucleotides which contain the desired sequence.

In addition, the invention also provides a recombinant vector which contains at least one copy of a recombinant DNA according to the present invention. Vectors which are suitable as a basis for protein expression in prokaryotic organisms are known to the expert. This vector is preferably one which allows a high expression of the recombinant DNA according to the present invention. The recombinant DNA on the vector is preferably under the control of an inducible expression signal (e.g. .lambda., tac, lac or trp promoter).

The vector according to the present invention can be present extrachromosomally (e.g. plasmid) or can be integrated in the genome of the host organism (e.g. bacteriophage lambda). The vector according to the present invention is preferably a plasmid. Vectors which are suitable in each case for gene expression in a particular host organism are known to one skilled in the art of molecular biology. It can be a eukaryotic vector, but preferably is a prokaryotic vector. Examples of suitable vectors for the expression of the DNA according to the present invention in prokaryotes are, for instance, commercially available pUC and pUR vectors.

The invention also provides a cell, preferably a prokaryotic cell, particularly preferably an *E. coli* cell, which is transformed with the recombinant DNA according to the present invention or/and with a recombinant vector according to the present invention.

When the fusion protein is expressed in prokaryotes, sparingly soluble aggregates (refractile bodies, inclusion bodies) are formed which are inactive. Therefore the fusion protein must be transformed into its active form. Using procedures which are familiar to those skilled in the art (cf. e.g. EP-A 0 219 874, EP A 0 114 506, WO 84/03711), first a solubilization is carried out by addition of denaturing agents which is followed by renaturation and, if desired, further purification steps. The treatment of the fusion protein with IgA protease takes place after PEGylation of the fusion protein.

In PEGylation, PEG groups are attached to reactive primary 6-amino groups of lysine residues of the fusion protein and optionally the α-amino group of the N-terminal amino acid of the fusion protein. Such amino group attachment of PEG to proteins is well known in the art. For example, review of such methods is given by Veronese, F. M., Biomaterials 22 (2001) 405-417. According to Veronese, the attachment of PEG to primary amino groups of proteins can be performed by using activated PEG derivatives which perform an alkylation of said primary amino groups.

Activated PEG derivatives are known in the art and are described in, for example, Morpurgo, M., et al., J. Bioconjugate Chem. 7 (1996) 363-368 for PEG-vinylsulfone. Examples of such derivatives include iodo-acetyl-methoxy-PEG and methoxy-PEG-vinylsulfone. The use of these iodo-activated substances is known in the art and is described, e.g., by Hermanson, G. T., in Bioconjugate Techniques, Academic Press, San Diego (1996), pp. 147-148. Electrophilically-activated PEG derivatives such as alkoxybutyric acid succinimidyl esters of poly(ethylene glycol) ("lower alkoxy-PEG-SBA"), alkoxypropionic acid succinimidyl esters of poly (ethylene glycol) ("lower alkoxy-PEG-SPA"), and N-hydroxysuccinimide activated PEGs are preferred. Further examples of activated PEG derivatives which may be used in PEGylation include: alkylating PEG derivatives, for example PEG aldehyde, PEG-tresyl chloride or PEG epoxide; acylating PEG derivatives such as hydroxysuccinimidyl esters of carboxylated PEGs or PEGs in which the terminal hydroxy group is activated by chloroformates or carbonylimidazole; and PEGs with amino acid arms. Such derivatives can contain the so-called branched PEGs, whereby at least two identical or different PEG molecules are linked together by a peptidic spacer (preferably lysine) and, for example, bound to IGF-I or IGF-I variant as activated carboxylate of the lysine spacer. N-hydroxysuccinimidyl esters of PEG and, preferably, N-hydroxysuccinimidyl esters of methoxypoly(ethylene glycol) are preferred activated PEG derivatives. The use of succinimidyl esters to produce conjugates with proteins is disclosed in U.S. Pat. No. 5,672,662. An especially preferred activated PEG derivative for use in the present invention is an N-hydroxysuccinimidyl activated branched PEG ester (mPEG2-NHS).

In the examples below, some preferred reagents for the production of amino-reactive IGF-I or IGF-I variants are described. It is understood that modifications, for example, based on the methods described by Veronese, F. M., Biomaterials 22 (2001) 405-417, can be made in the procedures as long as the process results in lysine-PEGylated IGF-I or IGF-I variants according to the invention.

Lysine-PEGylated IGF-I or IGF-I variants according to the invention may be prepared by covalently reacting a primary lysine amino group of an IGF-I or IGF-I variant with a bifunctional reagent to form an intermediate with an amide linkage and covalently reacting the intermediate containing amide linkage with an activated poly(ethylene glycol) derivative to form a lysine-PEGylated IGF-I or IGF-I variant. In the foregoing process, the bifunctional reagent is preferably N-succinimidyl-S-acetylthiopropionate or N-succinimidyl-S-acetylthioacetate, and the activated poly(ethylene glycol)

derivative is preferably selected from the group consisting of iodo-acetyl-methoxy-PEG, methoxy-PEG-vinylsulfone, and methoxy-PEG-maleimide.

Any conventional method of reacting an activated ester with an amine to form an amide can be utilized. In the reaction of an N-hydroxysuccinimidyl ester of PEG with IGF-I or an IGF-I variant, the exemplified succinimidyl ester is a leaving group causing the formation of an amide bond between IGF-I or IGF-I variant and PEG.

The reaction conditions used in PEGylation have an influence on the relative amount of differently PEGylated IGF-I or IGF-I variants. By manipulating the reaction conditions (e.g., ratio of reagents, pH, temperature, protein concentration, time of reaction etc.), the relative amounts of the different PEGylated species can be varied. Preferably the reaction is performed in a buffered aqueous solution pH 8-10, optionally containing up to 30% (v/v) ethanol. The molar protein:PEG ratio is preferably 1:1 to 1:6, preferably 1:2 to 1:5. Reaction temperature and reaction time can be varied according to the knowledge of a skilled artisan, whereby high temperature and long reaction time results in increased PEGylation. If monoP-EGylated proteins are desired, it is preferred to work between 4° C. and 22° C. and for up to 30 minutes or up to 60 minutes. When PEG or an activated PEG derivative is combined with IGF-I or IGF-I variant in a reaction buffer which preferably consists of 50 mM sodium borate and 25% ethanol at a pH of about 9.0-9.5, a protein:PEG ratio of about 1:3 to 1:4, and a reaction temperature of 4° C., a mixture of mono-, di-, and trace amounts of the tri-PEGylated species is produced depending on the presence of lysine residues in the protein.

The conditions required for the treatment of PEGylated IGF-I or IGF-I variant to be cleaved with IgA proteases are not critical. In this process it is, however, preferred that the ratio by weight of PEGylated IGF-I or IGF-I variant to IgA protease is 1:1 to 500:1, preferably, 100:1. The reaction preferably takes place in a buffered aqueous solution of pH 6.5 to 8.5. The buffer concentration is preferably in the range between 50 and 500 mmol/l if desired, with addition of 0-100 mmol/l sodium chloride. The cleavage is preferably carried out at room temperature for at least 60 min up to 5 days, preferably between 24 and 72 hours.

After solubilization, renaturation, PEGylation and cleavage with IgA protease, the PEGylated cleavage product obtained in this way is preferably purified by means of ion exchange chromatography, hydrophobic interaction chromatography and/or fractionation by size. The PEGylated IGF-I or IGF-I variant produced in this way is free of methionine at the N-terminus, preferably free of other proteins, like non-PEGylated IGF-I or IGF-I variant, and preferably free of N-terminal PEGylated propeptide, by 5%(w/w) or lower.

In preferred embodiments of the present invention, the IGF-I or IGF-I variant is mono-PEGylated or di-PEGylated. As used herein, the term "mono-PEGylated" means that the IGF-I or IGF-I variant has one PEG group attached thereto and the term "di-PEGylated" means that the IGF-I or IGF-I variant has two PEG groups attached thereto.

The invention also provides lysine-PEGylated IGF-I and lysine-PEGylated IGF-I variants as produced using the aforementioned method. Such lysine-PEGylated IGF-I or IGF-I variants contain linear or branched PEG randomly attached thereto, whereby the overall molecular weight of all PEG groups in the lysine-PEGylated IGF-I or IGF-I variant is preferably about 20 to about 80 kDa. It is obvious to a person skilled in the art that small deviations from this range of molecular weight are possible as long as the PEGylated IGF-I or IGF-I variant does show activity in lowering Abeta peptide levels in the brain. Also IGF-I and IGF-I variants wherein the overall molecular weight of all attached PEG groups is more than 80 kDa have higher bioavailability. However, it is expected that such activity decreases as the molecular weight increases due to reduced IGF-I receptor activation and blood-brain barrier transport. Therefore, the range of 20 to 100 kDa for the overall molecular weight of all attached PEG groups has to be understood as the optimized range for a lysine-PEGylated IGF-I or IGF-I variant useful for an efficient treatment of a patient suffering from Alzheimer's disease. As stated above, such a lysine-PEGylated IGF-I or lysine-PEGylated IGF-I variant does not contain an N-terminal methionine.

Preferably produced is a monoPEGylated IGF-I variant, selected from the group consisting of RKK (SEQ ID NO: 26), RKR (SEQ ID NO: 27) and RRK (SEQ ID NO: 28) wherein the branched PEG group has a molecular weight of 30-45, preferably 40-45 kDa (about 920 ethylene glycol units). For example, based on an average molecular weight of 44 kDa for PEG and a molecular weight of 7.6 kDa for IGF-I, the calculated average molecular weight for such a monoPEGylated IGF-I is about 51.6 kDa. Especially preferred is the use of an N-hydroxysuccinimidyl activated branched PEG ester (mPEG2-NHS) of a molecular weight of 40 kDa (Monfardini, C., et al., Bioconjugate Chem. 6 (1995) 62-69; Veronese, F. M., et al., J. Bioactive Compatible Polymers 12 (1997) 197-207; U.S. Pat. No. 5,932,462). Also preferably produced is a monoPEGylated IGF-I wherein the PEG has an average molecular weight of 30 or 40 kDa.

The following PEGylated forms of IGF-I or IGF-I variants are preferred products and available by the methods according to the invention:

a monoPEGylated IGF-I variant, preferably RRK (SEQ ID NO: 28) or RKK (SEQ ID NO: 26), more preferably RRK (SEQ ID NO: 28), wherein the PEG group has a molecular weight of 20 to 80 kDa (460 to 1840 ethylene glycol units) and is attached to the lysine at residue position 68;

a monoPEGylated IGF-I variant, preferably RKR (SEQ ID NO: 27) or RKK (SEQ ID NO: 26), more preferably RKR (SEQ ID NO: 27), wherein the PEG group has a molecular weight of 20 to 80 kDa (460 to 1840 ethylene glycol units) and is attached to the lysine at residue position 65;

a diPEGylated IGF-I variant, preferably RKK (SEQ ID NO: 26), wherein the PEG groups have a molecular weight of about 10-50 kDa (230 to 1150 ethylene glycol units) each and are attached to the lysines at residue positions 65 and 68;

a monoPEGylated IGF-I variant, preferably RRK (SEQ ID NO: 28) or RKK (SEQ ID NO: 26), more preferably RRK (SEQ ID NO: 28), comprising a PEG2 group having a molecular weight of 40 kDa attached to the lysine at residue position 68;

a monoPEGylated IGF-I variant, preferably RKR (SEQ ID NO: 27) or RKK (SEQ ID NO: 26), more preferably RKR (SEQ ID NO: 27), comprising a PEG2 group having a molecular weight of 40 kDa attached to the lysine at residue position 65;

a monoPEGylated IGF-I, wherein the PEG group has a molecular weight of 20 to 80 kDa (460 to 1840 ethylene glycol units);

a diPEGylated IGF-I, wherein the PEG groups have a molecular weight of about 10-50 kDa (230 to 1150 ethylene glycol units) each; and a monoPEGylated IGF-I, comprising a PEG 2 group having a molecular weight of 40 kDa.

Preparations of PEGylated IGF-I or IGF-I variants are substantially homogeneous. The preparation may contain small amounts of unreacted (i.e., lacking PEG group) protein. As ascertained by peptide mapping, purity of the variant is at least 90%(w/w). Further purification of such preparations, including the separation of mono- and/or diPEGylated IGF-I or IGF-I variants, can be performed by usual purification methods, preferably by size exclusion chromatography, hydrophobic interaction chromatography and/or by ion exchange chromatography, especially by cationic exchange chromatography.

The PEGylated IGF-I or IGF-I variant produced according to the invention provides improved stability in the circulation enabling a sustained access to IGF-I receptors throughout the body with low application intervals.

The compounds of the present invention can be formulated according to methods for the preparation of pharmaceutical compositions, which methods are known to the person skilled in the art. For the production of such compositions, a PEGylated IGF-I or IGF-I variant according to the invention is combined in a mixture with a pharmaceutically acceptable carrier, preferably by dialysis or diafiltration against an aqueous solution containing the desired ingredients of the pharmaceutical compositions. Such acceptable carriers are described, for example, in Remington's Pharmaceutical Sciences, 18th edition, 1990, Mack Publishing Company, edited by Oslo et al. (e.g. pp. 1435-1712). Typical compositions contain an effective amount of the substance according to the invention, for example from about 0.1 to about 100 mg/ml, together with a suitable amount of a carrier. The compositions may be administered parenterally. The PEGylated IGF-I or IGF-I variant according to the invention is administered preferably via intraperitoneal, subcutaneous, intravenous or intranasal application.

The pharmaceutical formulations according to the invention can be prepared according to known methods in the art. Usually, solutions of PEGylated IGF-I or IGF-I variant are dialyzed or diafiltrated against the buffer intended to be used in the pharmaceutical composition and the desired final protein concentration is adjusted by concentration or dilution.

The present invention relates also to a method for the treatment of Alzheimer's disease comprising the administration of a pharmaceutically-effective amount of lysine-PEGylated IGF-I or lysine-PEGylated IGF-I variant (as described above) to a patient in need of such treatment. In a preferred embodiment, the lysine-PEGylated IGF-I or lysine-PEGylated IGF-I variant is administered in an amount of from about 0.1 to about 100 mg/ml.

The following examples and figures are provided to aid the understanding of the present invention, the true scope of which is set forth in the appended claims. It is understood that modifications can be made in the procedures set forth without departing from the spirit of the invention. Names of the amino acids are abbreviated using either the one letter code (e.g. R) or the three letter code (e.g. Arg).

EXAMPLES

Example 1

The Following Mutants (Comprising IGF-I-Variant RRK) with the Propeptides of the animo acid sequence Met-$X_1$-His$_n$-$X_2$-Pro-Z were Produced) (PRPP disclosed as SEQ ID NO: 29):

| Mutant | $X_1$ | $X_2$ | n | Y |
|---|---|---|---|---|
| Px3036_IAG K27R K65R K68 (SEQ ID NO: 2) | none | KAKRFKKH (SEQ ID NO: 6) | 6 | PRPP |
| Px3036_IAG_R K27R K65R K68 (SEQ ID NO: 2) | none | RARRFRRH (SEQ ID NO: 7) | 6 | PRPP |

-continued

| Mutant | $X_1$ | $X_2$ | n | Y |
|---|---|---|---|---|
| Px3036_IAEE_F1 K27R K65R K68 (SEQ ID NO: 3) | S | NTEHNREH (SEQ ID NO: 8) | 6 | PRPP |
| Px3036_IAFX_F1 K27R K65R K68 (SEQ ID NO: 4) | N | IEGRH (SEQ ID NO: 9) | 6 | PRPP |
| Px3036_IAFX_F2 K27R K65R K68 (SEQ ID NO: 5) | N | TEFENIEH (SEQ ID NO: 10) | 6 | PRPP |

Preparation of IGF-I-variant (RRK variant) monoPEGylated at Residue Position 68

The expression vector and the *E. coli* strain used are described in EP 0 972 838. From an *E. coli* clone, expressing fusion protein px3036_IAG_R K27R K65R K68, px3036_IAEE_F1 K27R K65R K68, px3036_IAFX_F1 K27R K65R K68 or px3036_IAFX_F2 K27R K65R K68, grown on selective agar plate, one inoculating loop was transferred to (100 ml) selective medium and cultivated for 13 h at 37° C. to an optical density (578 nm) of 2-4. This culture was stored on ice for the next 6 hours prior to the automated inoculation of the main culture which was performed at 37° C. The expression of IGF-I mutant was initiated at an optical density (578 nm) of 50 with the addition of 1.0 mM IPTG. The overall fermentation lasted up to 16 hours. The amount of protein was determined densitometrically by comparing the volumetric intensity of the protein band of the product with the band of an IGF standard on a SDS-PAGE gel. The culture broth was harvested by centrifugation.

To obtain purified inclusion body (IB) material, the harvested biomass out of standard fermentation was treated with the following procedure: biomass was resuspended with TrisMgSO$_4$ buffer pH7 and supplemented with 0.3 g/100 g bio dry weight. Lysozyme and 5 U/1 g bio dry weight Benzonase were incubated for 20 min and homogenized. 30 U/1 g bio dry weight Benzonase was added and incubated for 60 min. at 37° C. 0.5 L Brij-buffer/liter was added and incubated for 30 min. at RT. After centrifugation the pellet was resuspended in 300 ml Tris-EDTA-buffer/100 g bio wet weight (purified IB wet weight), incubated for 30 min. at RT and centrifugated. 1 g IBs/liter were solubilized at room temperature in 6.8 M guanidine-HCl, 0.1 M TrisHCl, 0.1 M DTT, pH 8.5 overnight. The turbid solution was dialyzed at 4° C. against 6.8 M guanidine-HCl, 0.1 M TrisHCl, pH 8.0. After dialysis insoluble components were removed by centrifugation. Folding was performed by 50-fold dilution of the pro-IGF-I solution into 0.8 M arginine, 0.1 M TrisHCl, 0.1 M guanidine-HCl, 1 mM GSH, 1 mM GSSG, pH 8.5 at room temperature. After two hours the solution was supplemented with 2 M sodium chloride, filtered and applied at a flow rate of 10 ml/min to a HIC column (Butyl Sepharose 4 Fast Flow; GE, Amersham Biosciences), which had been equilibrated at room temperature with buffer containing 2 M NaCl, 0.8 M arginine, 0.1 M TrisHCl, 0.1 M guanidine-HCl, pH 8.5. The column was washed with equilibration buffer till baseline was achieved and then eluted with ten column volumes of a linear gradient starting with equilibration buffer and ending with buffer containing 0.1 M TrisHCl, 5% ethylene glycol, pH 8.5. Eluted fractions were analyzed by reversed phase high performance chromatography (rpHPLC). Fractions that contained protein with correctly formed SS-bridges were pooled.

Figure 2:
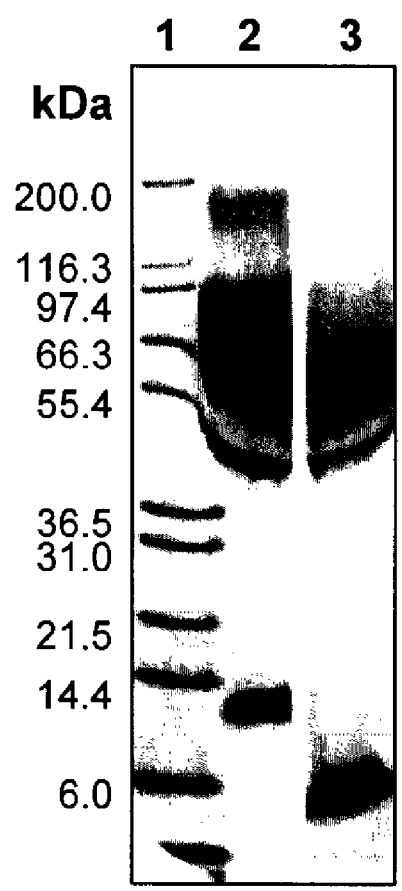
FIG. 2: Peptide analysis of monoPEGylated IGF-I variant.
SDS-PAGE analysis of pegylated fusion protein before and after IgA cleavage. Lane 1, mixture of standard protein (same as in FIG. 1); lane 2, reaction mix before IgA protease cleavage; lane 3, reaction mix after IgA protease cleavage.
Figure 3:
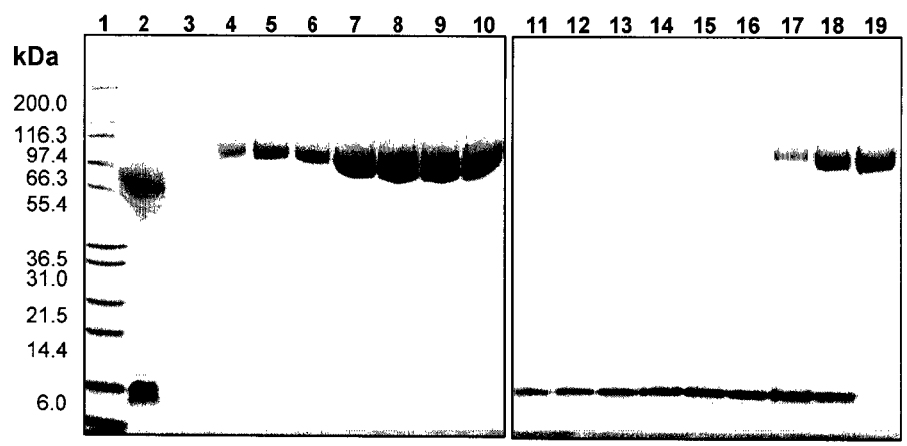
FIG. 3: SDS PAGE.
SDS-PAGE analysis of folded fusion protein before and after PEGylation. Lane 1, mixture of standard protein (same as in FIG. 1); lane 2, reaction mix before IEC; lane 3, flow through of IEC; lanes 4-19, single eluted fractions from IEC.

The pool was dialyzed at 4° C. against 50 mM sodium borate, pH 9.0. NHS activated 40 kDa branched PEG (N-hydroxysuccinimide (NHS) ester of mPEG MW 20'000 (mPEG2NHS, U.S. Pat. No. 5,932,462, Nektar Shearwater Polymers, Huntsville, Ala.) was solubilized in ice-cold 2 mM HCl and immediately added to the dialyzed protein solution (molar PEG-reagent / protein ratio 2:1). After 1 h and 2 h incubation on ice the same amount of acidic mPEG2-NHS solution was added to the protein/PEG reaction mix. After a third addition of the same amount of acidic mPEG2-NHS solution (overall 6-fold molar excess of PEG reagent) the reaction was incubated on ice for an additional hour. The reaction was stopped by the addition of solid ammonium chloride and incubation for another 45 minutes and then adjusted to pH 8.0 (see FIG. 1). The protein/PEG reaction mix was supplemented with IgA1 protease from *Neisseria gonorrhoea* (type 2) (w/w ratio 1:50) and incubated over night at room temperature (see FIG. 2). The reaction mix was diluted 1:2 with 50 mM acetic acid pH 4.5 and then applied to a cation IEC column (MacroCap SP support; GE, Amersham Biosciences, Uppsala, Sweden), which had been equilibrated with 50 mM acetic acid. The column was washed till baseline was reached and then eluted with 20 column volumes of a linear gradient starting with 50 mM acetic acid and ending with 50 mM acetic acid supplemented with 1 M sodium chloride. Eluted fractions were analyzed by SDS-PAGE. Fractions containing a single band with an estimated relative molecular size of about 60 kDa were pooled as IGF-I monoPEGylated at residue position 68 (see FIG. 3). Identity of IGF-I monoPEGylated at residue position 68 was verified by analytical size exclusion chromatography (SEC) with static light scattering detection, MS analysis of tryptic digests, MS analysis of Asp-N digests and analytical cation IEC. No other pegylation isovariant besides IGF-I monoPEGylated at residue position 68 could be found.

Example 2

The Following Mutants (Comprising IGF-I-Variant RKR) with the Propeptides of the amino acid sequence Met-$X_1$-His$_n$-$X_2$-Pro-Z are Produced):

| Mutant | $X_1$ | $X_2$ | n | Y |
|---|---|---|---|---|
| Px3036_IAG K27R K65 K68R (SEQ ID NO: 22) | none | KAKRFKKH | 6 | PRPP |
| Px3036_IAG_R K27R K65 K68R (SEQ ID NO: 22) | none | RARRFRRH | 6 | PRPP |
| Px3036_IAEE_F1 K27R K65 K68R (SEQ ID NO: 23) | S | NTEHNREH | 6 | PRPP |
| Px3036_IAFX_F1 K27R K65 K68R (SEQ ID NO: 24) | N | IEGRH | 6 | PRPP |
| Px3036_IAFX_F2 K27R K65 K68R (SEQ ID NO: 25) | N | TEFENIEH | 6 | PRPP |

Preparation of IGF-I-variant (RKR variant) monoPEGylated at Residue Position 65

The expression vector and the *E. coli* strain for use are described in EP 0 972 838. From an *E. coli* clone, expressing fusion protein px3036_IAG_R K27R K65 K68R, px3036_IAEE_F1 K27R K65 K68R, px3036_IAFX_F1 K27R K65 K68R or px3036_IAFX_F2 K27R K65 K68R, grown on selective agar plate, one inoculating loop is transferred to (100 ml) selective medium and cultivated for 13 h at 37° C. to an optical density (578 nm) of 2-4. This culture is stored on ice for the next 6 hours prior to the automated inoculation of the main culture which is performed at 37° C. The expression of IGF-I mutant is initiated at an optical density (578 nm) of 50 with the addition of 1.0 mM IPTG. The overall fermentation lasts up to 16 hours. The amount of protein is determined densitometrically by comparing the volumetric intensity of the protein band of the product with the band of an IGF standard on a SDS-PAGE gel. The culture broth is harvested by centrifugation.

To obtain purified inclusion body (IB) material, the harvested biomass out of standard fermentation is treated with the following procedure: biomass is resuspended with TrisMgSO4 buffer pH7, and supplemented with 0.3 g/100 g bio dry weight Lysozyme and 5 U/1 g bio dry weight Benzonase are incubated for 20 min and homogenized. 30 U/1 g bio dry weight Benzonase is added and incubated for 60 min. at 37° C. 0.5 L Brij-buffer/liter is added and incubated for 30 min. at RT. After centrifugation the pellet is resuspended in 300 ml Tris-EDTA-buffer/100 g bio wet weight (purified IB wet weight), incubated for 30 min. at RT and centrifugated. 1 g IBs/liter are solubilized at room temperature in 6.8 M guanidine-HCl, 0.1 M TrisHCl, 0.1 M DTT, pH 8.5 overnight. The turbid solution is dialyzed at 4° C. against 6.8 M guanidine-HCl, 0.1 M TrisHCl, pH 8.0. After dialysis insoluble components are removed by centrifugation. Folding is performed by 50-fold dilution of the pro-IGF-I solution into 0.8 M arginine, 0.1 M TrisHCl, 0.1 M guanidine-HCl, 1 mM GSH, 1 mM GSSG, pH 8.5 at room temperature. After 2 to 48 hours, preferably after 2 to 24 hours the solution is supplemented with 2 M sodium chloride, filtered and applied at a flow rate of 10 ml/min to a HIC column (Butyl Sepharose 4 Fast Flow; GE, Amersham Biosciences), which is equilibrated at room temperature with buffer containing 2 M NaCl, 0.8 M arginine, 0.1 M TrisHCl, 0.1 M guanidine-HCl, pH 8.5. The column is washed with equilibration buffer till baseline is achieved and then eluted with ten column volumes of a linear gradient starting with equilibration buffer and ending with buffer containing 0.1 M TrisHCl, 5% ethylene glycol, pH 8.5. Eluted fractions are analyzed by reversed phase high performance chromatography (rpHPLC). Fractions that contained protein with correctly formed disulfide-bridges are pooled. The pool is dialyzed at 4° C. against 50 mM sodium borate, pH 9.0. NHS activated 40 kDa branched PEG (N-hydroxysuccinimide (NHS) ester of mPEG MW 20'000 (mPEG2NHS, U.S. Pat. No. 5,932,462, Nektar Shearwater Polymers, Huntsville, Ala.) is solubilized in ice-cold 2 mM HCl and immediately added to the dialyzed protein solution (molar PEG-reagent/ protein ratio 2:1). After 1 h and 2 h incubation on ice the same amount of acidic mPEG2-NHS solution is added to the protein/PEG reaction mix. After a third addition of the same amount of acidic mPEG2-NHS solution (overall 6-fold molar excess of PEG reagent) the reaction is incubated on ice for an additional hour. The reaction is stopped by the addition of solid ammonium chloride and incubation for another 45 minutes and then adjusted to pH 8.0 (see FIG. 1). The protein/ PEG reaction mix is supplemented with IgA1 protease from Neisseria gonorrhoea (type 2) (w/w ratio 1:50) and incubated over night at room temperature (see FIG. 2). The reaction mix is diluted 1:2 with 50 mM acetic acid pH 4.5 and then applied to a cation IEC column (MacroCap SP support; GE, Amersham Biosciences, Uppsala, Sweden), which is equilibrated with 50 mM acetic acid. The column is washed till baseline is reached and then eluted with 20 column volumes of a linear gradient starting with 50 mM acetic acid and ending with 50 mM acetic acid supplemented with 1 M sodium chloride. Eluted fractions are analyzed by SDS-PAGE. Fractions containing a single band with an estimated relative molecular size of about 60 kDa are pooled as IGF-I monoPEGylated at residue position 65. Identity of IGF-I monoPEGylated at residue position 65 is verified by analytical size exclusion chromatography (SEC) with static light scattering detection, MS analysis of tryptic digests, MS analysis of Asp-N digests and analytical cation IEC.

Example 3

Reduction of Brain Soluble Abeta by IGF-I-Variant RRK MonoPEGylated at Residue Position 68 In vivo For evaluation of potency of IGF-I variant RRK monoPEGylated at residue position 68 (40 kD, PEG2) (PEG-RRK) on lowering soluble Abeta levels, 9-10 months old B6152H mice (doubletransgenic mice expressing human APP and PS2 mutants) with heavy amyloid plaque load were repeatedly treated by twice-a-week s.c. injection of 5 µg/kg PEG-RRK.

Figure 4:
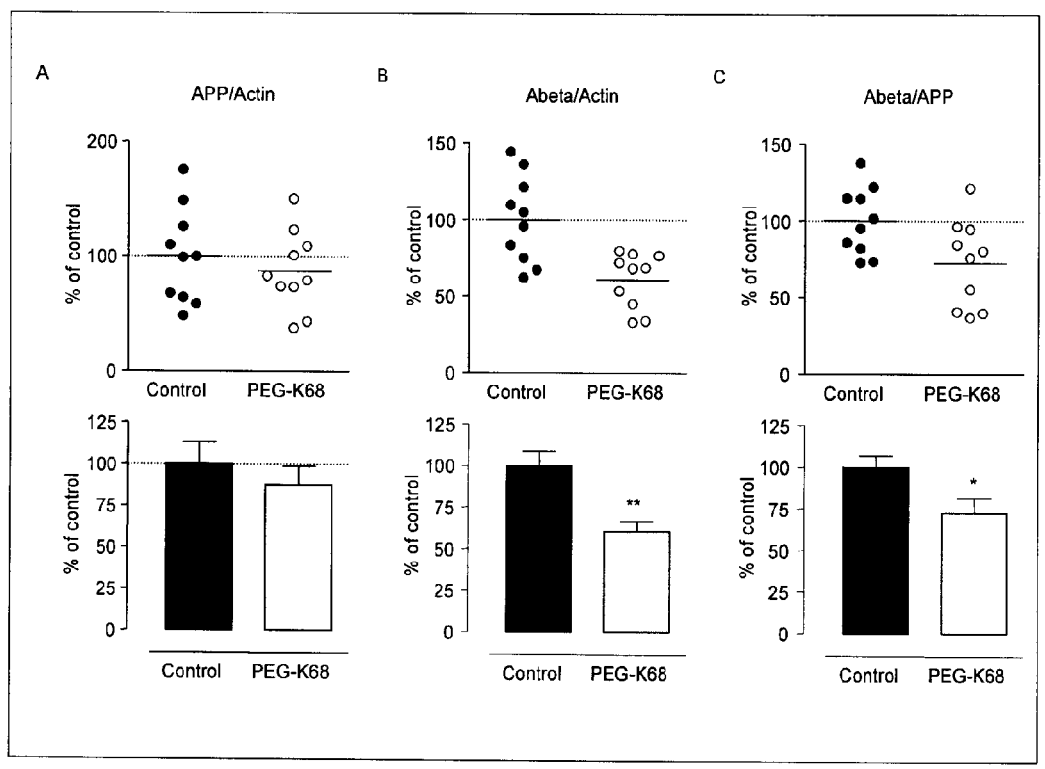
FIG. 4: In vivo brain Abeta lowering of PEG-RRK in B6152H mice.
Double-transgenic B6152H mice aged 9-10 months were treated with vehicle (NaCl) or with PEG-RRK (5 µg/kg s.c., twice-a-week) for 14 days. Soluble brain extracts were prepared and APP, Abeta and Actin levels evaluated as described. The ratios APP/Actin, Abeta/Actin and Abeta/APP were calculated, are expressed as % of control. A, APP/Actin; B, Abeta/Actin, C, Abeta/APP. Upper graphs show single animal data points, lower graphs show bar representation (means±SEM) including statistical differences (*, $p<0.05$; **, $p<0.01$ vs. untreated control, n=10).

Cortical APP, Abeta and Actin levels were detected after 14 days. The APP/actin ratio was not significantly changed by PEG-RRK (FIG. 4A) suggesting that PEG-RRK had no effect on transgene expression over 14 days. In contrast, Abeta/Actin (FIG. 4B) and Abeta/APP (FIG. 4C) ratios were significantly lowered by PEG-RRK. This indicates a positive effect of PEG-RRK on Abeta clearance independent on its production by the transgene.

The invention claimed is:

1. A fusion protein comprising insulin-like growth factor I (IGF-I) (SEQ ID NO: 1) or an IGF-I variant N-terminally linked to the C-terminus of a propeptide, said C-terminus of said propeptide comprising the amino acid sequence Y-Pro, wherein Y is selected from the group consisting of: Pro; Pro-Ala; Pro-Gly; Pro-Thr; Ala-Pro; Gly-Pro; Thr-Pro; Arg-Pro; Pro-Arg-Pro; Ala-Pro-Arg-Pro (SEQ ID NO: 12); and Pro-Ala-Pro-Arg-Pro (SEQ ID NO: 13) and said variant being a polypeptide which differs from SEQ ID NO: 1 in that one or two of the lysine residues at positions 27, 65, or 68 thereof is independently substituted by a polar amino acid selected from the group consisting of: cysteine; aspartic acid; glutamic acid; histidine; asparagine; glutamine; arginine; serine; and threonine; and the remainder of the amino acid sequence of said variant is the same as that of SEQ ID NO:1.

2. A method for the production of a lysine-PEGylated insulin-like growth factor I (IGF-I) or a lysine PEGylated IGF-I variant, said method comprising the steps of:
   (A) cultivating a prokaryotic host cell comprising an expression vector containing a nucleic acid encoding a fusion protein according to claim 1 and causing said cell to express said fusion protein;
   (B) recovering and lysine-PEGylating said fusion protein;

(C) cleaving said lysine-PEGylated fusion protein with IgA protease, and (D) recovering said lysine-PEGylated IGF-I or lysine-PEGylated IGF-I variant.

3. A method according to claim 2 wherein said lysine-PEGylated IGF-I or lysine-PEGylated IGF-I variant is mono-PEGylated or di-PEGylated.

4. A method according to claim 2 wherein said overall weight of all PEG groups in the lysine-PEGylated IGF-I or lysine-PEGylated IGF-I variant is from 20 to 100 kDa.

5. A method according to claim 2 wherein said PEG group or groups is/are branched.

6. A method according to claim 2 wherein said lysine-PEGylated IGF-I variant is selected from the group consisting of:

(A) a variant which comprises lysine at residue position 65 and is PEGylated at that position;

(B) a variant which comprises lysine at residue position 68 and is PEGylated at that position; and (C) a variant which comprises lysine at residue positions 65 and 68 and is PEGylated at those positions.

7. A method according to claim 2 wherein said lysine-PEGylated IGF-I variant is selected from the group consisting of:

(A) A polypeptide consisting of SEQ ID NO: 27 monoPEGylated at the lysine at residue position 65; and (B) A polypeptide consisting of SEQ ID NO: 28 monoPEGylated at the lysine at residue position 68.

8. A method according to claim 2 wherein said lysine-PEGylated IGF-I variant is a polypeptide consisting of SEQ ID NO: 26 and is monoPEGylated at the lysine present at residue position 65 or the lysine present at residue position 68 or is diPEGylated at the lysines present at residue positions 65 and 68.

9. A method according to claim 2 wherein said PEGylation is accomplished by reacting said fusion protein with a N-hydroxysuccinimidyl activated branched PEG ester.

* * * * *